United States Patent [19]
Piechocki et al.

[11] Patent Number: 5,660,731
[45] Date of Patent: Aug. 26, 1997

[54] FILTER FOR SEPARATING PHOTOACTIVE AGENT

[75] Inventors: Duane Piechocki, Pleasantville; Thomas J. Bormann, Melville; Vlado I. Matkovich, Glen Cove, all of N.Y.

[73] Assignee: PALL Corporation, East Hills, N.Y.

[21] Appl. No.: 337,365

[22] Filed: Nov. 8, 1994

[51] Int. Cl.$^6$ .................................................. B01D 15/00
[52] U.S. Cl. ............................ 210/669; 210/694; 435/2
[58] Field of Search ................................ 210/669, 694, 210/782, 787, 806; 435/2, 238

[56] References Cited

U.S. PATENT DOCUMENTS

| | | | |
|---|---|---|---|
| 3,989,740 | 11/1976 | Broussard et al. | 260/486 R |
| 4,880,548 | 11/1989 | Pall et al. | 210/767 |
| 4,925,572 | 5/1990 | Pall | 210/767 |
| 4,944,884 | 7/1990 | Naoi | 210/692 |
| 4,950,665 | 8/1990 | Floyd | 514/222.8 |
| 5,100,564 | 3/1992 | Pall et al. | 210/782 |
| 5,217,627 | 6/1993 | Pall et al. | 210/767 |
| 5,229,012 | 7/1993 | Pall et al. | 210/767 |
| 5,258,126 | 11/1993 | Pall et al. | 210/767 |
| 5,288,605 | 2/1994 | Lin et al. | 435/902 |
| 5,342,752 | 8/1994 | Platz et al. | 435/2 |
| 5,360,734 | 11/1994 | Chapman et al. | 435/238 |
| 5,418,130 | 5/1995 | Platz et al. | 435/2 |

FOREIGN PATENT DOCUMENTS

| | | |
|---|---|---|
| 0635068 | 4/1991 | Australia. |
| 2104296 | 9/1992 | Canada. |
| 0196515 | 10/1986 | European Pat. Off.. |
| 0246541 | 11/1987 | European Pat. Off.. |
| 9013296 | 11/1990 | WIPO. |
| 9117809 | 11/1991 | WIPO. |
| 9211059 | 7/1992 | WIPO. |
| 9215274 | 9/1992 | WIPO. |
| 9300005 | 1/1993 | WIPO. |
| 9317553 | 9/1993 | WIPO. |
| 9407426 | 4/1994 | WIPO. |
| 9500631 | 1/1995 | WIPO. |
| WO9516348 | 6/1995 | WIPO. |

OTHER PUBLICATIONS

Mohr, H. et al., "Virus Inactivated Single–Donor Fresh Plasma Preparations", Infusiontherapie, 1992: 79–83 (1992).

Lambrecht, B. et al., "Photoinactivation of viruses in human fresh plasma by phenothiazine dyes . . . ", Vox Sang, 60:207–213, 1991.

Hayes, J.S., Jr., "Novoloid and Related Fibers in Nonwoven Structures", American Kynol, Inc., Geneva, Apr. 20, 1993.

Hayes, J.S., Jr., "Activated Carbon Fibers and Textiles–Properties and Applications", American Kynol, Inc., New York, Jun. 1994.

Kuraray promotional material, "Activated Carbon Fiber Kuractive" Kuraray Chemical Company, Ltd., Japan (No date).

"HemaSure to collaborate with German Red Cross on Viral Inactivation Technology", CCBC Newsletter, Jul. 8, 1994, p. 9.

"Method of inactivation of viral blood contaminants using acridine deriatives", Heads Up, MicroPatent, Sep. 8, 1994.

"Swiss Red Cross collaborating with HemaSure . . . ", Heads Up PR Newswire, Aug. 30, 1994.

Primary Examiner—Ivars Cintins
Attorney, Agent, or Firm—Leydig, Voit & Mayer

[57] ABSTRACT

Methods, systems, and devices for removing methylene blue from a biological fluid are disclosed.

15 Claims, 2 Drawing Sheets

FILTER FOR SEPARATING PHOTOACTIVE AGENT

TECHNICAL FIELD

This invention relates to the processing of a biological fluid, preferably blood or blood components, to remove a photoactive material such as methylene blue.

BACKGROUND OF THE INVENTION

The presence of deleterious or undesirable material such as potentially pathogenic material such as viruses and/or bacteria in biological fluid is of great concern during many protocols, particularly those involving the processing of blood and/or blood components, e.g., to prepare transfusion products to be administered to a patient. For example, the introduction of disease causing material such as microorganisms, viruses and/or endotoxins into a patient, e.g., through administration of a contaminated fluid, may have serious, and possibly fatal, ramifications for the patient.

Additionally, those who handle the contaminated fluid and/or care for the patient may also face health risks resulting from exposure to the pathogens. Furthermore, the presence of microorganisms and/or viruses may adversely affect cell cultures and/or pose a health threat to laboratory technicians who handle the contaminated fluid or the fluid processing equipment.

Accordingly, a variety of protocols have been proposed to kill and/or inactivate potentially pathogenic material in biological fluid. Some protocols for inactivating microorganisms such as viruses and/or bacteria include exposing the material to light (or other forms of radiation), in the presence of an inactivating agent such as psoralen or methylene blue. It is believed that these inactivating agents are photoactive, so that in the presence of light they will react with the membrane structures and/or nucleic acids of the material in such a manner that the material, e.g., viruses and/or bacteria, may be killed, or prevented from replicating. With respect to reacting with the nucleic acids, it is believed that the photoactive agent cross-links to and/or damages the nucleic acids. It is also believed that some photoactive agents cause the conversion of molecular oxygen to oxygen radicals which are highly reactive and may have virucidal effects.

In some countries, some of these inactivating agents have been approved as licensed products that may be administered to a patient. Accordingly, material (e.g., blood or a blood component) treated with an inactivating agent may be administered to the patient without removing the agent. Apparently, since some regulations allow the administration of an inactivating agent to a patient, the art has not generally addressed the removal or separation of the agent from the material to be administered.

However, while some regulations may expressly allow the administration of an inactivating agent, this agent is "foreign" to the recipient's system, and it would be preferable to remove it before administering the material to a patient. Additionally, since inactivating agents are thought to bind to and/or damage nucleic acids, i.e., DNA and RNA, and damage to nucleic acids could lead to mutations, and possibly disease and/or birth defects, it would be desirable to minimize a patient's exposure to agents that could bind and/or damage nucleic acids.

There are other protocols that involve the removal or depletion of deleterious or undesirable material from biological fluids that could be beneficially combined with a protocol for inactivating and/or killing material such as viruses and/or bacteria. For example, since blood and blood components may include varying numbers of white blood cells (leukocytes), which may cause undesirable effects when administered to a patient, blood processing techniques may also include leukocyte depleting the blood or blood components, e.g., by passing the blood or blood components through a leukocyte depletion device. Since blood may also include potentially pathogenic material such as bacteria and/or viruses, it would be advantageous to provide a killing and/or inactivation procedure that is compatible with a leukocyte depletion protocol.

The present invention provides for ameliorating at least some of the disadvantages of the prior art protocols for treating blood. These improvements, and other advantages of the present invention, will be apparent from the description as set forth below.

SUMMARY OF THE INVENTION

In accordance with the present invention, at least one photoactive material such as methylene blue is removed or separated from a biological fluid by contacting the photoactive material with a photoactive agent binding arrangement comprising carbon fibers. In a more preferred embodiment, methods, devices and systems according to the instant invention provide for removing methylene blue from a biological fluid. In some embodiments, other undesirable material(s), particularly leukocytes, are also removed from the biological fluid.

The present invention is compatible with a variety of fluid treatment protocols that include the use of photoactive agents for inactivating material such as viruses and/or bacteria. For example, a biological fluid such as blood or a blood component may be contacted with a photoactive agent such as methylene blue, and the photoactive agent may be separated from the biological fluid by contacting the agent with a photoactive agent binding arrangement comprising carbon fibers. The photoactive agent binding arrangement preferably includes a porous medium including activated carbon fibers, and the photoactive agent may be bound or removed as the agent contacts the porous medium.

Even more preferably, a device including an inlet and an outlet and defining a fluid flow path between the inlet and the outlet, and having a binding arrangement comprising a porous medium including activated carbon fibers located between the inlet and the outlet and across the fluid flow path binds or removes the photoactive agent as the agent-containing fluid passes through the device. The biological fluid, now depleted of photoactive agent, is suitable for administration to a patient. In some embodiments, leukocytes are removed from the biological fluid, before, after, or while the photoactive agent is separated from the fluid.

In describing the present invention, the following terms are used as defined below.

(A) Biological Fluid. In accordance with the invention, biological fluid includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelets suspended in plasma, platelet concentrate (PC), platelet-rich plasma (PRP), platelet-free plasma, platelet-poor plasma (PPP), plasma, packed red cells (PRC), transition zone material, buffy coat; analogous blood products derived from blood or a blood component or derived from bone marrow; red cells suspended in physiological fluid; and platelets suspended in physiological fluid. The biological fluid may include leukocytes, or may be treated to remove leukocytes. As used herein, biological fluid refers to the components described above, and to similar blood products obtained by other means and with similar properties.

(B) Photoactive agent. A photoactive agent is a material that undergoes a chemical reaction when activated by radiation, e.g., light. Preferably, the photoactive agent is activated in the presence of at least one nucleic acid, i.e., DNA and/or RNA, and the chemical reaction leads to damage and/or binding with the nucleic acid. Typical photoactive agents include, but are not limited to at least one of porphyrins, and their derivatives; furocoumarins such as psoralens; phthalocyanines, such as aluminum phthalocyanine; merocyanines such as MC540; and other photoactive dyes such as acridine; xanthene dyes, e.g., rose bengal and eosin Y, and thiazine dyes, such as phenothiazine dyes. In one embodiment, the photoactive agent may comprise a drug such as a member of the family of light-activated drugs derived from benzoporphyrin. These derivatives are sometimes referred to as BPDs. In a more preferred embodiment, the photoactive dye is a thiazine dye, such as, but not limited to, at least one of thionine, toluidine blue, neutral red, and even more preferably, methylene blue.

The photoactive agent may be activated by visible light, sunlight, ultraviolet radiation, light emitting diodes, and other forms of radiation.

The preferred photoactive agent, methylene blue, is 3,7-Bis(dimethylamino)phenothiazin-5-ium chloride, $C_{16}H_{18}ClN_3S$. It is FDA approved for topical, intravenous, and oral administration, and has been reported to be effective as an antiseptic, disinfectant, and an antidote for cyanide and nitrate poisoning. However, while methylene blue is FDA approved for administration, methylene blue in the presence of light has been reported to damage DNA, probably by damaging or cleaving the DNA at the guanine residues.

SPECIFIC DESCRIPTION OF THE INVENTION

In accordance with the present invention, a method for processing a biological fluid comprises separating at least one photoactive agent such as methylene blue from the biological fluid by contacting a photoactive agent binding arrangement comprising carbon fibers with the photoactive agent. In an even more preferred embodiment, a biological fluid containing methylene blue is passed through the photoactive agent binding arrangement to remove the methylene blue from the biological fluid. The biological fluid, depleted of methylene blue, is suitable for further treatment or processing, e.g., administration to a patient. In some embodiments, the method also includes depleting the biological fluid of leukocytes. In one preferred embodiment, the methylene-depleted biological fluid includes plasma proteins.

Embodiments of the method may include contacting the biological fluid with the photoactive agent, exposing the fluid and photoactive agent to radiation, particularly light, and then separating the photoactive agent from the biological fluid by placing the agent in contact with a photoactive agent binding arrangement.

According to the present invention, a device for processing a biological fluid is provided comprising a photoactive agent binding arrangement including a porous medium capable of binding methylene blue, wherein said medium comprises carbon fibers and is compatible with the biological fluid. In a preferred embodiment, the photoactive agent binding arrangement includes two or more layers wherein at least one layer includes carbon fibers. In an even more preferred embodiment, a device according to the invention comprises a housing having an inlet and an outlet and defining a fluid flow path between the inlet and the outlet, and including the photoactive binding arrangement between the inlet and the outlet and across the fluid flow path.

Each of the components of the invention will now be described in more detail below.

PHOTOACTIVE AGENT BINDING ARRANGEMENT

The photoactive agent binding arrangement 10, which includes carbon fibers, is capable of binding at least one photoactive agent when the agent is placed in contact with the binding arrangement. In a preferred embodiment, the binding arrangement 10 provides for substantially complete removal of the photoactive agent, i.e., the amount of photoactive agent that may be present is below the minimum detectable by conventional protocols routinely utilized in the art, including, for example, high pressure liquid chromatography (HPLC) and spectrophotometry.

Figure 1:
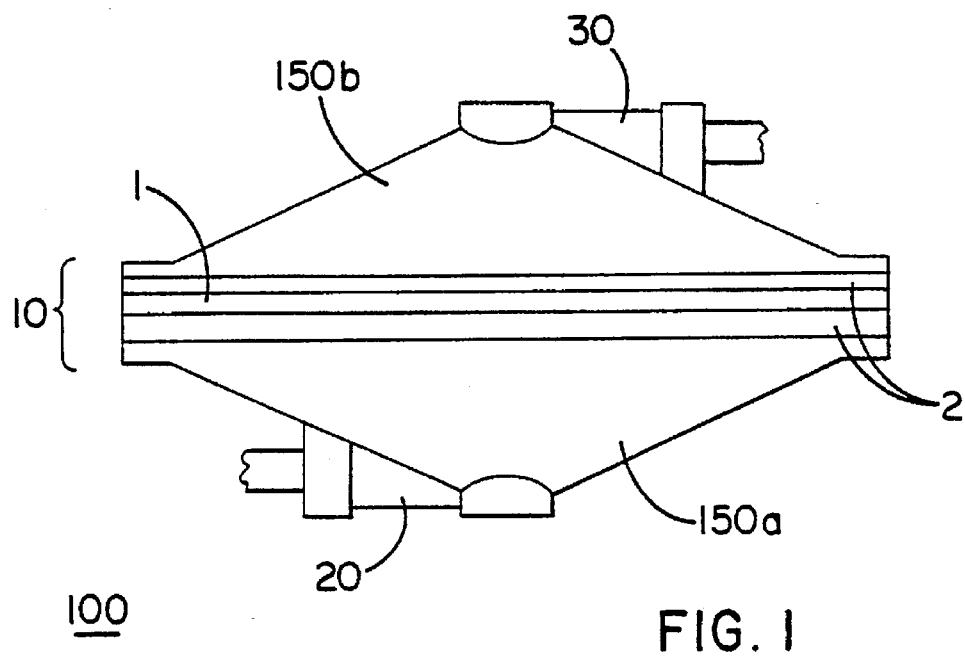
FIG. 1 is an embodiment of the present invention including a photoactive binding arrangement in a housing.

Typically, as illustrated in FIG. 1, the photoactive agent binding arrangement 10 may be arranged within a housing. For example, in a preferred embodiment, as illustrated in FIG. 1, device 100 comprises a housing having a first portion 150a including an inlet 20, and a second portion 150b including an outlet 30, and defining a fluid flow path between the inlet and the outlet, with the photoactive agent binding arrangement 10 arranged across the flow path between the inlet 20 and the outlet 30. Accordingly, as a biological fluid containing at least one photoactive agent such as methylene blue is passed through the device, photoactive agent contacts the binding arrangement, and is separated from the biological fluid.

In accordance with the invention, the photoactive agent binding arrangement 10 includes a medium 1 including carbon fibers, preferably activated carbon fibers. In one embodiment, the photoactive agent binding arrangement 10 comprises a medium 1 which includes a porous medium including a plurality of activated carbon fibers which are themselves porous. In an even more preferred embodiment, the medium 1 comprises a self-supporting medium including activated carbon fibers. In one embodiment, the carbon fiber-containing medium 1 also includes other media, e.g., non-carbon fibers.

The binding arrangement may have a variety of configurations, including, for example, one or more of the following: a web, sheet, a cylinder, and a depth filter. Of course, in some embodiments, for example, including at least one web, the configuration may also provide for depth filtration. Preferably, the binding arrangement includes a planar, rather than pleated, configuration. However, the arrangement may be formed into any geometric shape or form suitable for contacting a biological fluid. More preferably, the binding arrangement is in a shape or form suitable for passing a biological fluid containing at least one photoactive agent through the arrangement.

The arrangement may include two or more layers and/or media. Layers and/or media may be fibrous and/or membranous. Layers and/or media may provide prefiltration, support and/or better drainage.

The binding arrangement may comprise layers and/or media each having a different pore structure.

In a preferred embodiment, wherein the binding arrangement 10 includes activated carbon fibers that are porous, the pore structure of each fiber may refer to, for example, the pore radius or the pore half-width within the carbon fiber. The pore radius and the pore half-width may be determined and/or calculated as is known in the art.

However, a medium including a plurality of carbon fibers may itself have a different pore structure, e.g., a pore size, or a pore rating, or a pore diameter, since the pore structure of the medium could refer to, for example, the distance between the fibers, the ability of the medium to remove particles of a specified size, and/or the efficiency in removing particular material. Preferably, the pore structure of the medium provides for passage of plasma proteins therethrough.

The photoactive agent binding arrangement 10 includes a carbon fiber-containing medium 1 that preferably adsorbs at least one photoactive agent. Suitable carbon fiber-containing media 1 include activated carbon fiber-containing media, e.g., activated carbon felts, and cloths. Examples of commercially available activated carbon media include Kuractive® media, available from Kuraray Chemical Company, Ltd., Bizen City, Japan; and novoloid fibers, e.g., Kynol™ novoloid fibers available from Nippon Kynol (Japan) and American Kynol, Inc. (Pleasantville, N.Y.).

In accordance with the invention, the binding arrangement comprises carbon fibers, more preferably, activated carbon fibers. Fibers provide a large available surface area and provide an increased adsorption capacity, so that more photoactive agent can be depleted from the biological fluid. Additionally, as will be noted in more detail below, the use of carbon fibers, particularly the use of a self-supporting medium including carbon fibers, provides for more efficient processing of the biological fluid, and/or allows the use of a smaller, more compact device. Moreover, a device including a self-supporting medium including carbon fibers lends itself to more economical manufacturing, due to, for example, the integrity and/or unitary nature of the self-supporting medium as compared to carbon particles. Illustratively, a self-supporting medium including carbon fibers may be more easily sealed in a housing, since the possibility of a poor seal to due carbon particles settling or shifting into the sealing area while sealing is eliminated.

A photoactive agent binding arrangement 10 comprising a self-supporting medium including carbon fibers, more particularly, a felt of activated carbon fibers, may allow more efficient processing of the biological fluid, since, for example, the differential pressure may be less than when processing the fluid through a bed of carbon particles. Illustratively, an arrangement including carbon fibers may be more open than an arrangement including particles, so that fluid flows through the arrangement more easily, and the pressure drop is relatively low. In contrast, a bed of carbon particles may include sections and/or portions that are more inaccessible to the fluid to be passed therethrough, e.g., due to carbon particles packed together. Not only does this reduce the surface area capable of contacting the fluid, but the packing may cause an increased pressure drop as the fluid passes through the bed. Moreover, the use of a bed of carbon particles may allow fluid to bypass at least part of the bed, as the fluid is channeled along a preferential passageway created by the packed or settled particles.

Alternatively or additionally, embodiments including a self-supporting medium including activated carbon fibers may be advantageous when it is desirable to provide a more compact filter or device. For example, a photoactive agent binding arrangement comprising a self-supporting medium including carbon fibers arranged within a compact housing provides a large surface area and high adsorption capacity. Accordingly, the use of carbon fibers provides for efficient removal of the photoactive agent from the fluid, while allowing passage of desirable components of the biological fluid through the carbon fiber containing medium. Thus, embodiments of the present invention provide for substantially complete removal of the photoactive agent, e.g., methylene blue, from the fluid.

The desirable components of the biological fluid, e.g., at least one of red cells; platelets; plasma; and plasma proteins and coagulation factors such as at least one of fibrinogen, Factor I, Factor II, Factor V, Factor VII, Factor VIII, Factor IX, Factor X, Factor XI, Factor XII, plasminogen, antithrombin III, C1-inactivator, and prothrombin complex, which have been depleted of the photoactive agent, may be efficiently recovered in an amount suitable for further use.

In some embodiments, for example, involving the processing of a biological fluid including plasma proteins, e.g., processing plasma or fresh frozen plasma, a photoactive agent binding arrangement including activated carbon fibers provides efficient binding of at least one photoactive agent such as methylene blue, while allowing at least one desirable plasma protein to pass through the arrangement with little or no removal of the protein.

In one preferred embodiment, the arrangement provides for passing fibrinogen, Factor V, Factor VII, Factor VIII, Factor IX, and Factor XI, therethrough, with little or no removal of the proteins.

A typical total surface area of the activated carbon is greater than about 1000 $m^2/g$. For example, a preferred total surface area ranges from about 1500 to about 2500 $m^2/g$; more preferably, about 2000 $m^2/g$. While a range of fiber diameters are suitable, typically, fiber diameters are in the range of about 8 to about 10 microns.

With respect to the pore structure of each fiber, a preferred arrangement includes fibers having pores that are predominantly small, more preferably, pores having a substantially uniform size or size distribution. For example, a typical pore radius is greater than about 9 Å, e.g., about 12 to about 22 Å, or more. In one preferred embodiment, the pore radius is about 16 Å. The pore radius may be determined and/or calculated as is known in the art.

It has been hypothesized that the pores of an activated carbon fiber, or at least the pore openings, are slit shaped. Accordingly, it has been suggested, e.g, in *Activated Carbon Fibers and Textiles*, Properties and Applications, by Joseph S. Hayes, Jr., June, 1994, pages 1–20; and *Novoloid and Related Fibers in Nonwoven Structures*, by Joseph S. Hayes, Jr., Index 93 Congress Session 2C-Fibres, Geneva: Apr. 20, 1993, which are incorporated by reference in their entireties, that the term referring to the pore structure of activated carbon fibers should be "half-width" rather than "pore radius".

In one embodiment, the pores in the activated carbon fibers are predominantly micropores according to the methods and models of Hayes (in the papers referenced supra), i.e., pores having half-widths of less than about 1.5 nm. However, in other embodiments, the pores of the fibers may include macropores according to the methods and models of Hayes, i.e., pores with half-widths of over about 100 nm, and/or transitional pores (between micropores and macropores).

In some embodiments, as will be noted in more detail below, the photoactive agent binding arrangement, which includes carbon fibers, may additionally include at least one other medium. While the other medium or media may include carbon, and may bind or remove some amount of photoactive agent, this media, which is hereinafter referred to as "non-carbon" primarily serves to remove other substances or material, such as at least one of debris, microaggregates, and leukocytes. The non-carbon media may also provide, for example, filtration, support and/or drainage.

In a preferred embodiment, the arrangement also includes non-carbon media. Typically, a carbon fiber-containing medium may be upstream of a non-carbon medium such as at least one of polybutylene terephthalate (PBT), polyethylene terephthalate (PET) and nylon. In a more preferred embodiment, as illustrated in FIG. 1, the carbon fiber-containing medium 1 may be interposed between non-carbon media 2.

In some embodiments, the non-carbon medium 2 may provide at least one of support and/or drainage for at least one carbon fiber-containing medium. Alternatively or additionally, a non-carbon medium may provide for filtration, e.g., filtration downstream of the carbon medium, for example, to prevent carbon fines from reaching a patient, and/or prefiltration upstream of the carbon medium. The non-carbon medium may also provide for removal of undesirable material such as leukocytes.

While the non-carbon medium 2 may be produced from any suitable material compatible with the biological fluid, commercially available materials are preferred. The media of this invention may be preferably formed, for example, from any natural or synthetic material capable of forming fibers or a membrane. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene difluoride (PVDF), polyethylene, polypropylene, polybutylene terephthalate (PBT), polyethylene terephthalate (PET), and any nylon, e.g., Nylon 6, 11, 46, 66, and 610. Preferred polymers are polyolefins, polyesters, and polyamides. Especially preferred is polyester.

In accordance with the invention, the surface characteristics of the non-carbon medium may be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, or to various other forms of radiation, or by surface etching or deposition using a gas plasma treatment. The medium may be treated to modify the critical wetting surface tension (CWST). In a preferred embodiment, the medium has a CWST of greater than about 53 dynes/cm, more preferably, greater than about 60 dynes/cm.

In a preferred embodiment, as illustrated in FIG. 1, the binding arrangement 10 is arranged within a housing to form a filter device or assembly 100. The housing may be fabricated from any suitably rigid, impervious material, including any impervious thermoplastic material, which is compatible with the fluid being processed. For example, the housing may be fabricated from a metal, such as stainless steel, or from a polymer. In a preferred embodiment, the housing is fabricated by injection molding from a polymer, more preferably a transparent or translucent polymer, such as an acrylic, polypropylene, polystyrene, or a polycarbonated resin. Not only is such a housing easily and economically fabricated, but also it allows observation of the passage of the fluid through the housing. The housing may include one or more channels, grooves, conduits, passages, ribs or the like which may be serpentine, parallel or curved, or a variety of other configurations to provide for more efficient flow of fluid.

Any housing of suitable shape to provide an inlet, an outlet, and an adequate flow area may be employed.

A variety of techniques for sealing the binding arrangement 10 in the housing are suitable. For example, the arrangement may be sealed within the housing via insert molding; thermal-press sealing; welding, e.g., ultrasonic or heat welding; edge crimping; interference fit; and the like. Similarly, the first portion 150a and the second portion 150b of the housing may be sealed in any suitable manner as is known in the art.

The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

In some embodiments, the binding arrangement 10 may be utilized without using a housing. For example, at least one binding arrangement may be arranged within at least one container such as a blood collection or satellite bag such as may be used in commercially available blood processing sets and/or systems. Illustratively, at least one binding arrangement may be located within the bag so that the majority of fluid passes along a substantially defined fluid flow path through the arrangement. In other embodiments, the arrangement may be located so that the fluid contacts the arrangement without the fluid passing along a substantially defined flow path through the arrangement.

Figure 2:
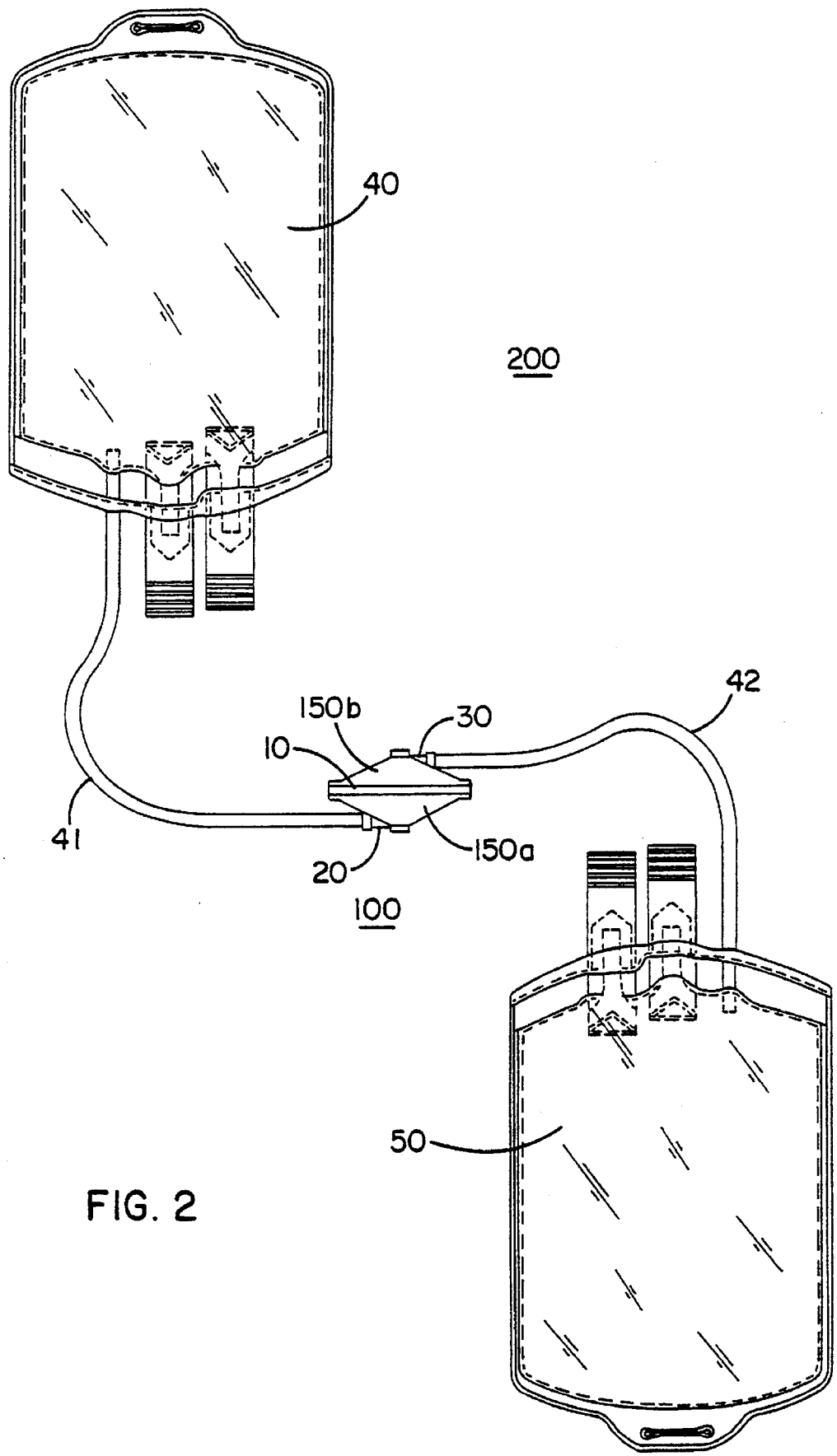
FIG. 2 is an embodiment of a system according to the present invention including a photoactive binding arrangement in a housing interposed between two containers.

Biological fluid, with or without photoactive agent, may be collected, recovered and/or stored in at least one container, such as containers 40 and 50 as illustrated in FIG. 2. While a variety of containers, including flexible and non-flexible containers, are suitable, in a preferred embodiment, the containers 40 and 50 are commercially available blood collection and/or satellite bags. In an even more preferred embodiment, at least one container is transparent, i.e., allows the contents of the container to be exposed to radiation. This embodiment is particularly advantageous for those embodiments that include exposing the biological fluid and photoactive agent in a container to radiation.

Typically, the biological fluid, with or without photoactive agent, is passed from one container to another via conduits, for example, commercially available flexible tubing, e.g., as used in conventional blood processing systems. For example, as shown in FIG. 2, conduits 41 and 42 provide fluid communication with photoactive agent binding filter device 100, interposed between containers 40 and 50.

In some embodiments, at least one conduit and/or container may have at least one photoactive agent contained therein. For example, at least one conduit may include at least one photoactive agent, e.g., sealed between a first end and a second end of the conduit. Additionally, or alternatively, at least one container may contain at least one photoactive agent. If desired, the conduit and/or container may be steam sterilizable. In some embodiments, a steam sterilizable conduit and/or container may comprise a non-PVC plastic material, e.g., at least one of polypropylene, styrene-ethylene-butylene-styrene (SEBS), ethylenevinyl acetate, polyester, and polyurethane.

A system in accordance with the present invention preferably includes a photoactive agent binding arrangement, at least one container, and at least one conduit. While the photoactive agent binding arrangement may be located within a container as described previously, in a more preferred embodiment, system 200 includes, as illustrated in FIG. 2, a device 100 comprising a housing having a first portion 150a including an inlet 20, and a second portion 150b including an outlet 30, and defining a fluid flow path between the inlet and the outlet, with the photoactive agent binding arrangement 10 arranged across the flow path between the inlet 20 and the outlet 30; wherein the device 100 is interposed between containers 40 and 50 via conduits 41 and 42. Accordingly, in accordance with an embodiment of the system, a photoactive agent-containing biological fluid may be passed from container 40 through the photoactive agent binding device 100 so that the photoactive agent contacts the carbon fiber-containing medium 1 of the binding arrangement 10, and the photoactive agent-depleted biological fluid may be recovered or collected in container 50.

A system 200 according to the invention may be open or closed. In a preferred embodiment, the system is closed and sterile. The system, which may be part of system for automated processing as disclosed in, for example, International Publication WO 94/01193, which is incorporated by reference in its entirety, is suitable for use with other devices including, for example, filters, especially leukocyte filter devices, and gas processing devices. Accordingly, the system may include, for example, at least one of a leukocyte depletion filter, a red cell barrier filter, and a combined leukocyte depletion red cell barrier filter as disclosed in, for example, U.S. Pat. Nos. 4,880,548; 4,925,572; 5,100,564; 5,152,905; 5,217,627; 5,229,012; 5,258,126; as well as International Publication Nos. WO 93/25295 and WO 93/04763. Alternatively or additionally, the system may included gas processing devices such as gas inlets and/or gas outlets as disclosed in U.S. Pat. Nos. 5,126,054 and 5,217, 627; and International Publication WO 91/17809, as well as gas collection and displacement devices as disclosed in International Publication No. WO 93/25295. All of the above referenced patents and International publications are incorporated by reference herein in their entirety.

In one embodiment, the system includes at least one leukocyte depletion filter and a photoactive agent binding filter, and at least two containers, with conduits allowing fluid communication between the filters and containers.

In another embodiment, a system includes a red cell barrier filter or a combined red cell barrier/leukocyte depletion filter; a photoactive agent binding filter, and at least two containers, more preferably, at least three containers, with conduits allowing fluid communication between the filters and containers.

Figure 3:
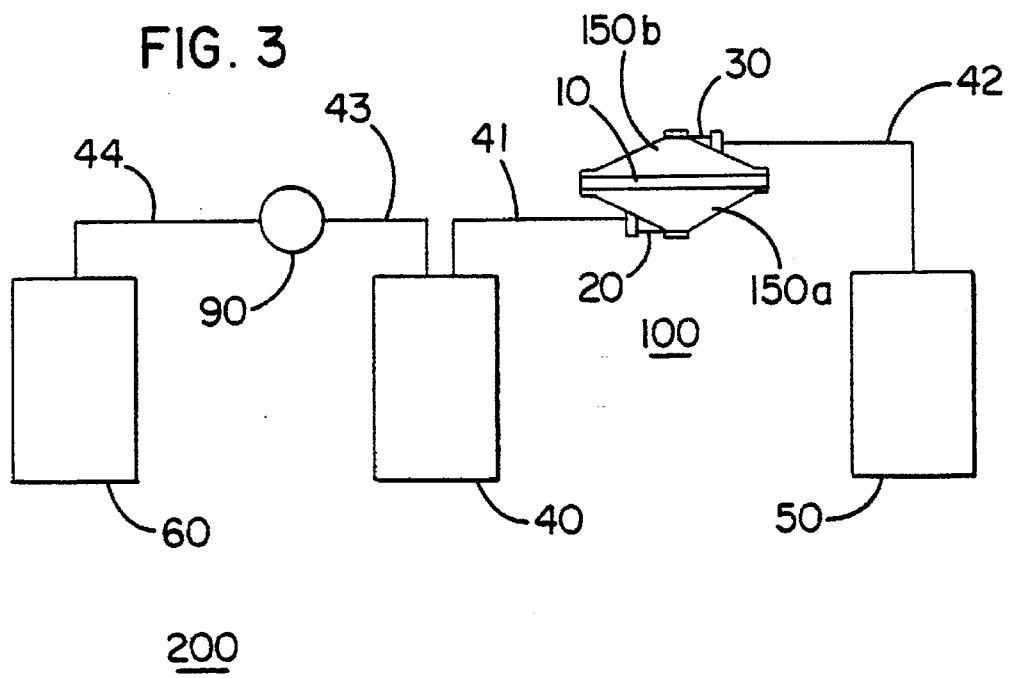
FIG. 3 is yet another embodiment of a system according the present invention.

In an embodiment, in accordance with a system 200 as illustrated in FIG. 3, red cell barrier filter or a combined red cell barrier/leukocyte depletion filter 90 is interposed between a first container 60 such as a collection bag or a satellite bag, and a second container 40 such as a satellite bag, and a photoactive agent binding device 100 is interposed between the second container 40 and a third container 50 such as a satellite bag. Conduits 41–44 provide fluid communication between the components of the system 200.

Preferably, a container and/or conduit upstream of the photoactive agent binding device includes at least one photoactive agent such as methylene blue.

Illustratively, systems, preferably, closed systems, for example, as illustrated in FIG. 3, including a red cell barrier filter or a combined red cell barrier leukocyte depletion filter 90; a photoactive agent binding device 100; and a plurality of containers 40, 50, and 60, allow a biological fluid such as whole blood to be processed to produce, for example, concentrated red cells, buffy coat, and platelet-free or platelet-poor plasma, wherein at least the platelet-free or platelet-poor plasma is exposed to at least one photoactive agent, and the photoactive agent is removed from the plasma. In some embodiments, the system includes at least one additional container having at least one photoactive agent such as methylene blue therein.

In accordance with a method provided by the invention, at least one photoactive agent such as methylene blue is separated from a biological fluid using a photoactive agent binding arrangement including carbon fibers. For example, a photoactive agent containing biological fluid is placed in contact with the photoactive agent binding arrangement by passing the agent containing fluid through the binding arrangement, and the photoactive agent contacting the carbon fiber-containing medium of the binding arrangement is bound. Accordingly, the biological fluid is depleted of photoactive agent. The desirable components of the biological fluid which have been depleted of the photoactive agent, e.g., at least one of red cells; platelets; plasma; and plasma proteins and coagulation factors such as at least one of fibrinogen, Factor I, Factor II, Factor V, Factor VII, Factor VIII, Factor IX, Factor X, Factor XI, Factor XII, plasminogen, antithrombin III, C1-inactivator, and prothrombin complex, may be efficiently recovered in an amount suitable for further use.

In some embodiments, for example, involving the processing of a biological fluid including plasma proteins, e.g., processing plasma-containing fluid such as platelet-poor-plasma or fresh frozen plasma, the photoactive agent-containing biological fluid is placed in contact with the photoactive agent binding arrangement, and the photoactive agent is bound. The biological fluid, depleted of photoactive agent, is recovered, and the fluid includes at least one desirable plasma protein with little or no removal of the protein.

Illustratively, a plasma-containing biological fluid is placed in contact with at least one photoactive agent such as methylene blue, and the plasma- and methylene blue-containing biological fluid is passed through the photoactive agent binding arrangement. The biological fluid passing through the arrangement is depleted of methylene blue, with little or no removal of proteins such as fibrinogen, Factor V, Factor VII, Factor VIII, Factor IX, and Factor XI.

In one embodiment, a biological fluid containing methylene blue is passed through a photoactive agent binding arrangement including activated carbon fibers to separate the methylene blue from the biological fluid. In a preferred embodiment, a biological fluid containing methylene blue is passed through a photoactive agent binding device comprising a housing including an inlet and an outlet and defining a fluid flow path between the inlet and the outlet, and, having a photoactive agent binding arrangement comprising a self-supporting medium including activated carbon fibers, across the fluid flow path between the inlet and the outlet, to separate the methylene blue from the biological fluid.

The recovered methylene blue depleted biological fluid is suitable for further processing or treatment, e.g., fractionation and/or administration to a patient. In an even more preferred embodiment, leukocytes are removed from the biological fluid. For example, leukocytes may be removed before, after, or while passing the biological fluid through the photoactive agent binding arrangement.

In accordance with the invention, a typical embodiment of the method includes treating the biological fluid with at least one photoactive agent, i.e., contacting the biological fluid with at least one photoactive agent, and exposing the photoactive agent-containing biological fluid to radiation, e.g., light, to activate the agent. The photoactive agent is then separated from the biological fluid as described previously.

A variety of protocols for treating the fluid with at least one photoactive agent are known in the art, and the invention is not to be limited thereby.

Illustrative protocols for contacting the fluid with photoactive agent include adding at least one photoactive agent to the biological fluid, or by placing photoactive agent in a container and then passing the fluid into the container. The photoactive agent utilized, and other parameters (e.g., concentration of the agent, the amount of contact time before exposure to radiation) will depend upon the biological fluid to be treated and the characteristics of the photoactive agent used, as is known in the art.

Components of the biological fluid may be separated from each other before or after contacting the fluid with photoactive agent. For example, whole blood may be contacted with at least one photoactive agent, and then separated into components such as platelet free plasma, buffy coat, and packed red cells; or platelet rich plasma and packed red cells. Alternatively, whole blood may be separated into components, and at least one of the separated components may be contacted with at least one photoactive agent.

The biological fluid may be, for example, frozen and thawed before or after exposure to the photoactive agent. In some embodiments, freezing the biological fluid, e.g., plasma, lyses leukocytes present in the fluid, which may release material such as viruses which are contained in, or are associated with, the leukocytes. After the fluid is thawed, at least one photoactive agent may be placed in contact with the fluid so that subsequent activation of the agent while in contact with the fluid inactivates these released viruses. However, other embodiments of the method are carried out without releasing material, e.g., by freezing, before contacting the fluid with the inactivation agent. For example, as described below, the biological fluid may be depleted of leukocytes, e.g., by passing the fluid through a leukocyte depletion filter, or a combined red cell barrier/leukocyte depletion filter. Since the leukocytes are depleted from the biological fluid, the leukocyte associated material is also removed. Accordingly, the leukocyte-depleted fluid may be placed in contact with at least one photoactive agent without freezing the fluid before such contact.

The photoactive agent containing biological fluid may be exposed to radiation as is known in the art. Accordingly, the radiation source, the band of radiation utilized, and other parameters (e.g., radiation intensity, length of exposure period) will depend upon the biological fluid to be treated and the characteristics of the photoactive agent used. In some embodiments, a portion of the photoactive agent may be removed before exposing the remaining portion to radiation.

The biological fluid is subsequently depleted of photoactive agent as described previously, e.g., by placing the photoactive agent in contact with a photoactive agent binding arrangement. Typically, the biological fluid is depleted of photoactive agent as it is passed through a photoactive agent binding device. Illustratively, the biological fluid containing methylene blue is passed through the binding device at a flow rate in the range of from about 5 ml/min to about 100 ml/min. In a more preferred embodiment, the flow rate is in the range from about 10 ml/min to about 80 ml/min.

In some embodiments, the photoactive agent depleted biological fluid may be washed, filtered, and/or stored, before further use.

In a preferred embodiment of a method according to the invention, the biological fluid is also leukocyte depleted. For example, the fluid may be passed through a leukocyte depletion medium, more preferably, a fibrous leukocyte depletion medium, before, after, and/or while passing the fluid through the photoactive agent binding arrangement.

In an embodiment of the invention, the photoactive agent binding arrangement includes two or more layers, wherein at least one layer includes activated carbon fibers, and at least one layer includes a leukocyte depletion medium, so that the fluid passing through the arrangement may be depleted both of leukocytes and a photoactive agent such as methylene blue. In some embodiments, the photoactive agent binding arrangement includes a layer of activated carbon fibers interposed between layers of leukocyte depletion media. Such an configuration may provide for prefiltration (e.g., removal of microaggregates before the fluid contacts the carbon) as well as removal of photoactive agent and leukocytes. This configuration may also prevent carbon fines from passing through the photoactive agent binding device. Illustratively, as illustrated in FIG. 1, the photoactive agent binding arrangement 10 may include a carbon fiber containing porous medium 1 interposed between non-carbon media 2, wherein the non-carbon media comprise leukocyte depletion media.

As noted above, in some embodiments, the photoactive agent binding arrangement 10 may include leukocyte depletion media in addition to the carbon fibers. Of course, the photoactive agent binding device 100 may include at least one leukocyte depletion medium separate from the binding arrangement 10. Alternatively, or additionally, a method in accordance with the invention includes the use of at least one separate leukocyte depletion filter, e.g., in a separate housing. For example, biological fluid may be passed through a leukocyte depletion device before passing the fluid through a photoactive agent binding device.

For example, one embodiment of a method includes passing a biological fluid such as whole blood or a blood component through a leukocyte depletion filter into at least one downstream container, exposing the leukocyte depleted fluid to at least one photoactive agent, activating the photoactive agent in the presence of the blood, and removing the photoactive agent by passing the fluid through a photoactive agent binding device that is also capable of additionally leukocyte depleting the fluid. In another embodiment, a blood component such as plasma is leukocyte depleted, exposed to a photoactive agent, and, after activation of the agent, the agent is removed from the plasma by passing the plasma through a photoactive agent binding device.

With respect to FIG. 3, in one embodiment according to the invention, whole blood may be collected in container 60, and the blood may be processed, preferably by centrifugation, more preferably, hard spin centrifugation, to provide a supernatant layer including plasma, e.g., platelet-poor plasma, and a sediment layer including concentrated red cells. Typically, the sediment layer includes a substantial number of platelets, and a substantial number of leukocytes will be present in the buffy coat between the supernatant and sediment layers. The supernatant layer may be passed into container 40 through a red cell barrier filter assembly or a red cell barrier/leukocyte depletion filter assembly 90, so that the plasma collected in container 40 is substantially free of red blood cells.

In one embodiment, at least one photoactive agent such as methylene blue may be previously added to container 40, so that the plasma entering the container is exposed to the methylene blue. Alternatively, methylene blue from an additional container is passed to container 40 after the plasma is collected in container 40. The methylene blue is preferably activated in the presence of the plasma while in the container 40.

The methylene blue may be separated from the plasma when the plasma containing methylene blue is passed through the photoactive binding device 100, and the plasma, depleted of methylene blue, is collected in container 50.

Of course, as noted earlier, since the system may include at least one photoactive agent in a container or conduit, the blood, or at least one blood component, may be exposed to the photoactive agent at any desired point during processing. Since the conduits and containers are preferably transparent, the photoactive agent, e.g., may be activated when desired.

During the processing of biological fluid in accordance with the invention, with or without photoactive agent, air or gas may be present and/or fluid may be trapped or retained in various elements of the processing system. It may be desirable to minimize the presence of air or gas and/or to maximize the recovery of the retained biological fluid. Accordingly, at least one of a gas inlet, gas outlet, and a gas collection and displacement loop as disclosed in, for example, U.S. Pat. Nos. 5,126,054 and 5,217,627; and International Publication Nos. WO 91/17809, and WO 93/25295, may be used to separate gas from the biological fluid and/or to recover biological fluid trapped or retained in various elements of the system.

As noted earlier, in some embodiments, the photoactive agent may be placed in contact with the binding arrangement by, for example, placing the arrangement (e.g., without a housing) in a container including biological fluid and the photoactive agent. The fluid need not be passed along a defined fluid flow path through the binding arrangement to place the agent in contact with the binding arrangement and thereby bind the agent. Alternatively, or additionally, handling the container, e.g., transporting, inverting and/or rocking the container, may cause additional fluid and agent to contact the binding arrangement, and additional agent may be bound.

Accordingly, once the biological fluid and the binding arrangement are separated from one another, e.g., by passing the fluid to a separate container, and/or by removing the fluid from the container holding the binding arrangement, the biological fluid is depleted of photoactive agent.

EXAMPLES

EXAMPLE 1

A photoactive agent binding arrangement includes two approximately 50 mm diameter porous media (discs) of activated carbon fibers, with the two media placed one on top of the other and then interposed between layers of approximately 50 mm diameter discs of leukocyte depletion media comprising polybutylene terephthalate (PBT) fibers. Accordingly, the arrangement includes an upstream disc including PBT fibers, two discs including activated carbon fibers, and a downstream disc including PBT fibers.

The discs of activated carbon fibers are felts of activated carbon fibers made from phenolic fibers, having a total surface area of about 2000 $m^2/g$ after activation. The fibers have a pore radius of about 16 Å. The discs are available from Kuraray Chemical Company (Bizen City, Japan) under part no. FT-300-20.

The two discs of fibrous leukocyte depletion media (each comprising a single layer) are produced and radiation grafted in accordance with U.S. Pat. No. 4,880,548. The CWST is about 94 dynes/cm. The basis weight of each disc is about 5.2 $g/ft^2$; each disc has a thickness of about 0.02", and the fiber diameter is less than about 3 μm.

The four discs, i.e., an upstream layer of leukocyte depletion medium, the felts of activated carbon fibers, and the downstream layer of leukocyte depletion medium, are arranged within a housing as generally shown in FIG. 1, to form a methylene blue filter assembly. The filter assembly has a hold up volume of about 7 ml.

Approximately 218 ml of non-leukocyte depleted fresh platelet rich plasma (PRP) is placed in a plastic satellite bag. A stock solution of methylene blue at a concentration of 500 ppm (i.e., 5.3 mg of methylene blue in 10.6 ml of PRP) is prepared. 262 μL of this 500 ppm stock solution is added to the 218 ml of PRP to prepare a mixture having a methylene blue concentration of about 0.6 ppm. The plasma with methylene blue is greenish in color.

The bag of PRP containing methylene blue is connected to the inlet of the filter assembly, and an empty satellite bag is connected to the outlet of the filter assembly, via flexible tubing, as generally illustrated in FIG. 2. The filter assembly is positioned horizontally, as shown in FIG. 2, at a height between the plasma bag and the empty bag. The PRP is passed through the filter assembly and into the empty bag. The PRP entering the filter assembly is greenish in color, and the PRP exiting the methylene blue filter assembly is yellowish in color.

A Bausch and Lomb Spectronic Model 21D spectrophotometer is utilized to analyze the fluid before and after filtering. The spectrophotometer is calibrated using a sample of the original unfiltered PRP at a wavelength of 609 nm to zero the device. The absorbance of a sample of non-filtered PRP mixed with methylene blue and having a methylene blue concentration of about 0.6 ppm is determined to be 0.041. The absorbance of a sample of filtered PRP is determined to be less than the minimum detectable by the machine.

This Example shows that essentially all of the methylene blue present in a unit of PRP can be removed by a methylene blue filter assembly in accordance with the invention.

EXAMPLE 2

A filter assembly, including two felts of activated carbon fibers and leukocyte depletion media, sealed in a housing, is prepared as described in Example 1. A unit of fresh frozen plasma (FFP) is thawed, and methylene blue is added to the unit to prepare a mixture having a methylene blue concentration of about 0.6 ppm. The unit of thawed FFP containing methylene blue in a transparent container is exposed to light having a wavelength of about 660 nm for about 30 minutes, and then the container is moved away from the light source.

The unit of treated FFP is then passed through a filter assembly as described above at a flow rate of about 80 ml/min. The unit of plasma (post illumination) is sampled before and after passing through the filter assembly.

The samples are analyzed for concentrations of methylene blue. Additionally, the samples are analyzed for the presence of plasma proteins such as fibrinogen, Factor V, Factor VII, Factor VIII, Factor IX, and Factor XI. The analysis shows that the assembly removes all detectable amounts of methylene blue, and that the plasma proteins are not removed.

This Example shows that essentially all of the methylene blue present in a unit of thawed FFP can be removed by a methylene blue filter assembly in accordance with the invention, without removing substantial amounts of plasma proteins.

While the invention has been described in some detail by way of illustration and example, it should be understood that the invention is susceptible to various modifications and alternative forms, and is not restricted to the specific embodiments set forth. It should also be understood that these specific embodiments are not intended to limit the invention but, on the contrary, the intention is to cover all modifications, equivalents, and alternatives falling within the spirit and scope of the invention.

We claim:

1. A method for processing a biological fluid comprising:
   removing red blood cells from a biological fluid to produce a plasma protein-containing biological fluid that is substantially free of red blood cells;
   placing the plasma-protein containing biological fluid in contact with a photoactive agent;
   activating the photoactive agent;
   separating the photoactive agent from the plasma protein-containing biological fluid by passing the agent-containing fluid through a photoactive agent binding arrangement including carbon fibers; and
   recovering the plasma protein-containing biological fluid.

2. The method of claim 1 wherein separating the photoactive agent from the biological fluid comprises passing a methylene blue-containing biological fluid through the photoactive agent binding arrangement and separating methylene blue from the biological fluid.

3. The method of claim 2 wherein the photoactive agent binding arrangement comprises a self-supporting medium including activated carbon fibers.

4. The method of claim 3 wherein the plasma protein-containing biological fluid includes the plasma proteins, fibrinogen, Factor V, Factor VII, Factor VIII, Factor IX, and Factor XI, the method comprising passing the plasma proteins, fibrinogen, Factor V, Factor VII, Factor VIII, Factor IX, and Factor XI through the medium and removing substantially all of the methylene blue from the plasma protein-containing biological fluid.

5. The method of claim 2 including removing leukocytes from the biological fluid.

6. The method of claim 5 wherein passing the fluid through the arrangement comprises passing the fluid through a prefilter, and a medium including activated carbon fibers.

7. The method of claim 6 wherein the arrangement includes at least one leukocyte depletion medium.

8. The method of claim 1, wherein the plasma protein-containing biological fluid includes at least one of the plasma proteins selected from the group consisting of fibrinogen, Factor V, Factor VII, Factor VIII, Factor IX, and Factor XI, the method comprising passing at least one of the plasma proteins, fibrinogen, Factor V, Factor VII, Factor VIII, Factor IX, and Factor XI through a photoactive binding arrangement comprising a self-supporting medium including activated carbon fibers and removing substantially all of the photoactive agent from the plasma protein-containing biological fluid.

9. The method of claim 1, wherein the plasma protein-containing biological fluid includes the plasma proteins, fibrinogen, Factor V, Factor VII, Factor VIII, Factor IX, and Factor XI, the method comprising passing the plasma proteins, fibrinogen, Factor V, Factor VII, Factor VIII, Factor IX, and Factor XI through a photoactive binding arrangement comprising a self-supporting medium including activated carbon fibers and removing substantially all of the photoactive agent from the plasma protein-containing biological fluid.

10. The method of claim 1 wherein separating the photoactive agent from the plasma protein-containing fluid includes separating a chemical reaction product of the activated photoactive agent from the plasma protein-containing biological fluid by passing the photoactive agent and the chemical reaction product through a photoactive agent binding arrangement comprising a self-supporting medium including activated carbon fibers.

11. The method of claim 10 wherein the photoactive agent comprises methylene blue.

12. The method of claim 11 wherein the plasma protein-containing biological fluid includes at least one of the plasma proteins selected from the group consisting of factor II, fibrinogen, and factor X, the method comprising passing at least one of the plasma proteins, factor II, fibrinogen, and factor X through the photoactive agent binding arrangement.

13. The method of claim 10 wherein the plasma protein-containing biological fluid includes at least one of the plasma proteins selected from the group consisting of factor II, fibrinogen, and factor X, the method comprising passing at least one of the plasma proteins, factor II, fibrinogen, and factor X through the photoactive agent binding arrangement.

14. A method for processing a biological fluid comprising:
    passing a biological fluid including plasma-proteins and red blood cells to a red cell barrier filter or a combined red cell barrier leukocyte depletion filter;
    passing the plasma-protein containing fluid through said filter and into at least one container downstream of the filter, wherein the plasma protein-containing fluid in the downstream container is substantially free of red cells;
    placing the plasma protein-containing fluid in contact with at least one photoactive agent;
    activating the photoactive agent; and,
    separating the agent from the fluid by passing the photoactive agent-containing fluid through a photoactive agent binding arrangement including activated carbon fibers.

15. The method of claim 14 wherein the biological fluid comprises whole blood including red blood cells, plasma, plasma proteins, platelets, and leukocytes, and the method includes centrifuging the whole blood to form a sediment layer including red blood cells, and a supernatant layer including plasma proteins, before passing the plasma proteins and red blood cells to the red cell barrier filter or the combined red cell barrier leukocyte depletion filter.

* * * * *